United States Patent [19]

Bridgman

[11] 4,311,140
[45] Jan. 19, 1982

[54] VACUUM CURET HAVING AN IMPROVED CURETTING OPENING

[76] Inventor: Henry Bridgman, P.O. Box 71, Convent Station, N.J. 07961

[21] Appl. No.: 45,403

[22] Filed: Jun. 4, 1979

Related U.S. Application Data

[63] Continuation of Ser. No. 684,971, May 10, 1976, abandoned, which is a continuation-in-part of Ser. No. 381,740, Jul. 23, 1973, Pat. No. 3,955,579.

[51] Int. Cl.³ ............................................. A61M 1/00
[52] U.S. Cl. ..................................... 128/276; 128/304
[58] Field of Search ............................... 128/276, 304

[56] References Cited

U.S. PATENT DOCUMENTS

| | | | |
|---|---|---|---|
| 805,206 | 11/1905 | Jordan . | |
| 1,074,965 | 10/1913 | McClellan . | |
| 1,080,929 | 12/1913 | Romeo | 128/304 |
| 1,217,886 | 2/1917 | Hopkins . | |
| 1,222,424 | 4/1917 | Laurent . | |
| 1,360,809 | 11/1920 | Smith . | |
| 2,064,815 | 11/1936 | Armstrong . | |
| 2,346,841 | 4/1944 | Henderson | 128/276 |
| 2,397,257 | 3/1946 | Goland | 128/276 |
| 2,419,795 | 4/1947 | Saunders | 128/297 |
| 2,421,959 | 6/1947 | Norris | 128/276 |
| 2,465,685 | 3/1949 | Henderson | 219/44 |
| 2,539,846 | 1/1956 | Lewis et al. | 230/190 |
| 2,757,840 | 5/1956 | Weissenberg et al. | 226/20.1 |
| 2,819,718 | 1/1958 | Goldman | 128/350 R |
| 2,945,496 | 7/1960 | Fosdal | 128/276 X |
| 3,037,495 | 6/1962 | Naz | 128/2 |
| 3,074,396 | 1/1963 | MacLean | 128/2 |
| 3,111,145 | 11/1963 | Kerns | 141/26 |
| 3,143,109 | 8/1964 | Gewertz | 128/2 |
| 3,175,553 | 3/1965 | Mattson | 128/2 |
| 3,430,628 | 3/1969 | Wiggins | 128/276 |
| 3,491,748 | 1/1970 | Pate | 128/2 |
| 3,515,135 | 6/1970 | Flower | 128/145.6 |
| 3,528,404 | 9/1970 | Chan | 128/2 |
| 3,542,031 | 11/1970 | Taylor | 128/276 |
| 3,577,980 | 5/1971 | Cohen | 128/2 |
| 3,661,144 | 5/1972 | Jensen | 128/2 B |
| 3,661,144 | 5/1972 | Jensen et al. | 128/304 |
| 3,721,244 | 3/1973 | Elmaleh | 128/304 |
| 3,749,090 | 7/1973 | Stewart | 128/240 |
| 3,769,980 | 11/1973 | Karman | 128/304 |
| 3,774,612 | 11/1973 | Marco | 128/276 X |
| 3,774,613 | 11/1973 | Woods, Jr. et al. | 128/304 |
| 3,828,781 | 8/1974 | Rothman | 128/304 |
| 3,833,000 | 9/1974 | Bridgman | 128/276 |
| 3,835,843 | 9/1974 | Karman | 128/17 |
| 3,946,739 | 3/1976 | Berman et al. | 128/304 |
| 3,955,579 | 5/1976 | Bridgman | 128/276 |
| 4,055,167 | 10/1977 | Bernstein | 128/304 |

FOREIGN PATENT DOCUMENTS

| | | |
|---|---|---|
| 1444305 | 3/1966 | France . |
| 2018258 | 3/1970 | France . |
| 671942 | 5/1952 | United Kingdom . |
| 710272 | 6/1954 | United Kingdom . |
| 970646 | 9/1964 | United Kingdom . |
| 970647 | 9/1964 | United Kingdom . |
| 990808 | 5/1965 | United Kingdom . |
| 1070179 | 6/1967 | United Kingdom . |
| 1086822 | 10/1967 | United Kingdom . |
| 1180184 | 2/1970 | United Kingdom . |
| 1257044 | 12/1971 | United Kingdom . |
| 1262229 | 2/1972 | United Kingdom . |
| 1269405 | 4/1972 | United Kingdom . |
| 1297183 | 11/1972 | United Kingdom . |
| 1304324 | 1/1973 | United Kingdom . |
| 1316780 | 5/1973 | United Kingdom . |
| 1333347 | 10/1973 | United Kingdom . |

Primary Examiner—Robert W. Michell
Assistant Examiner—J. L. Kruter
Attorney, Agent, or Firm—Roland Plottel

[57] ABSTRACT

A vacuum curet having an improved curet tip opening. The curetting opening has a larger open cross section area than heretofore used and a novel shape. The shape includes (a) a central flat portion extending in a plane through the axis of the curet, (b) a cutting edge portion, at the distal end of said central portion, inclined slightly from a plane perpendicular to the axis of the curet toward the proximal end; and (c) a rounded non-cutting portion extending in a curved shape with a preferred radius from the near end of the central portion to the outside of the curet. Use in sampling tissue from the endometrium for diagnostic purpose.

14 Claims, 4 Drawing Figures

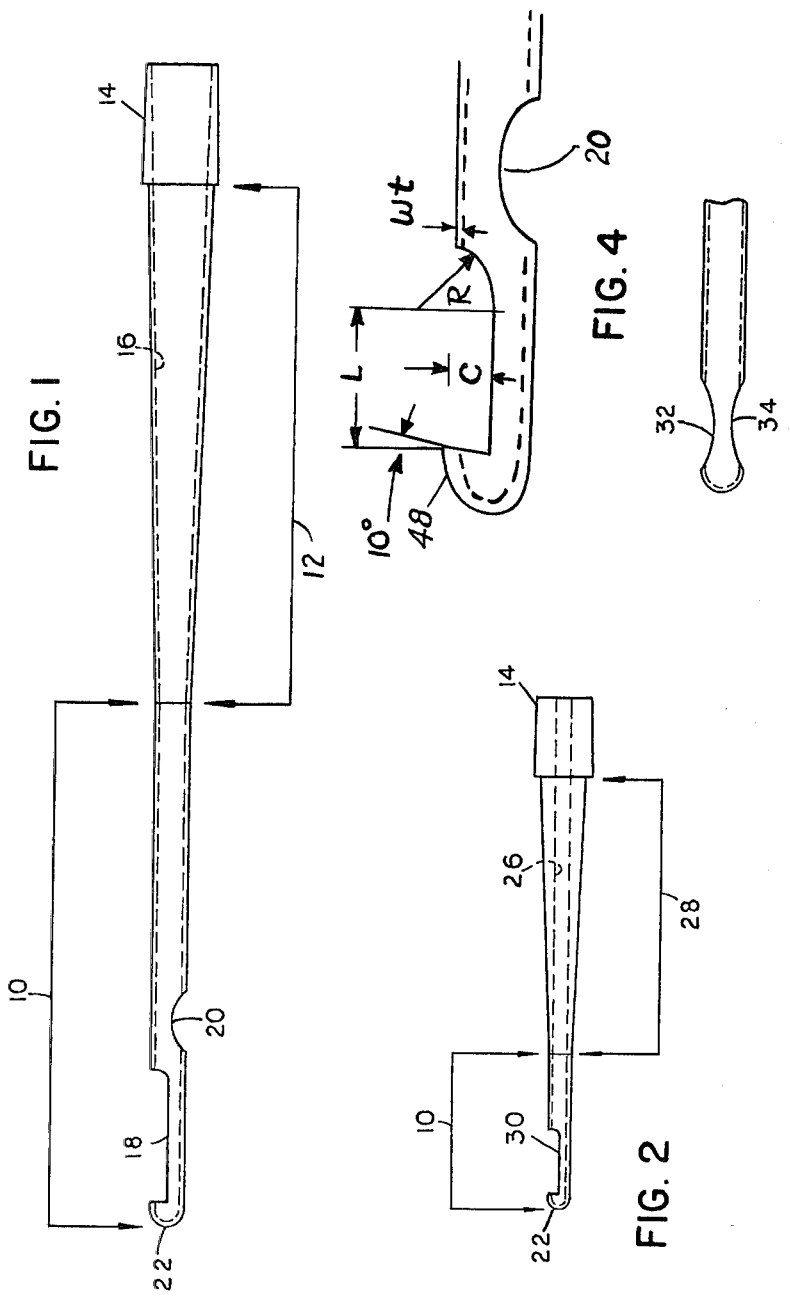

VACUUM CURET HAVING AN IMPROVED CURETTING OPENING

This application is a continuation of application Ser. No. 684,971 filed May 10, 1976, now abandoned, which was a continuation in part of application Ser. No. 381,740 filed July 23, 1973, now U.S. Pat. No. 3,955,579.

The invention relates generally to medical and surgical apparatus and particularly to vacuum curets.

Curets have been used for many years to remove fluids and/or tissue from the body. A typical curet is a hollow tube having openings at each end. One opening is attached to a source of vacuum, typically by a hose. The opposite end is introduced into that portion of the body from which fluid and/or tissue is to be removed. When the vacuum is applied, the fluids and/or tissue are removed through the hollow portion of the curet.

Examples of typical applications for vacuum curet procedures (vacuum curettage) includes (1) diagnostic, e.g. collecting tissue for endometrial diagnostics, such as polyps, atypia, or adenocarcinoma; (2) surgical, e.g. abortions during the early months of pregnancy; and (3) menstrual regulation.

Examples or prior art curets and surgical apparatus using these curets are shown and described in my U.S. Pat. No. 3,713,444—entitled Collection Bottle, and my co-pending U.S. Patent Application Ser. No. 258,960, filed on June 2, 1972, entitled Medical Aspiration System and Method. Reference may be made to those applications for illustrations of typical vacuum curettage procedures and complete vacuum curettage apparatus.

Curets have heretofore been made of stainless steel, bone and different plastics. If the curet is too rigid, there is the possibility, and the statistically observed fact, of undesirably piercing a membrane or wall in the body during a vacuum curettage procedure. If not rigid enough, the surgeon has difficulty in "feeling" what he is doing, and, where tissue is sampled, may not provide enough strength or leverage to obtain suitable specimens.

A specific example might be helpful. In uterine aspiration, the typical curet is 8 to 10 inches long. One end of the curret—which is attached to a source of suction and an adjacent intermediate portion which resides in the relatively wide vagina during the procedure—should be rigid. The other end of the curet—which is in the very narrow cervical canal protruding into the uterus during the procedure—should be (1) flexible to minimize the undesired possible perforation of the wall and (2) of a small diameter as possible to minimize the trauma associated with the cervix dilation. This diameter is determined by the procedure which dictates what the inside diameter, or flowthrough portion, of the curet must be. For certain procedures a minimum of 3½ mm are needed. For others, 10 mm may be needed. The only way to decrease the outer diameter of the curet is to make its walls as thin as possible over that portion in the cervical canal, and wider and more rigid in the intermediate and proximal portions, where size is not essential and more rigidity is needed. Prior art curets have not recognized this need, nor offered the solution of the present invention.

A second example illustrates a further aspect of the present invention: In the diagnostic sampling of endometrial tissue by a vacuum curettage, it is necessary that the aperture at the tip of the curet near the endometrial region have a sharp or cutting edge. This suggests a rigid curet. The curet itself must also be rigid enough to give the surgeon a "feel" as he moves the cutting tip of the curet over the endometrial surface. The curet, however, should also be flexible so as to avoid punching through the uterine wall. In the present invention, these problems have been identified and a novel tip opening and novel curet is provided which offers a solution thereto.

A difficulty heretofore attendant with prior art curets during vacuum curettage, especially in tissue sampling, was to reduce unnecessary blood loss and trauma to the sampling region and cervical canal. The curet of the present invention tends to minimize this blood loss and trauma.

A further aspect of the curet of the present invention is that it may be easily machine mass produced. Prior art curets of small internal diameter lumens were not capable of such manufacture. The curet of the present invention may be inexpensively mass produced and thus employed on a once-use-throw-away basis.

FIG. 1 is a plane view, not to scale, of one embodiment of the invention.

FIG. 2 is a plane view, not to scale, of an alternative embodiment of the invention.

FIG. 3, is a plane view, not to scale, of a portion of the distal end portion of a curet showing an alternative embodiment of the tip opening.

FIG. 4, is a side view of a portion of the distal end of the curet of FIG. 1, showing the tip opening in detail.

Referring now to FIG. 1, there is shown a plane view of the curet, constructed in accordance with the invention. The curet is not drawn to scale, but is exaggerated in certain dimensions to point-up various features. The curet is described herein with specific illustrative dimensions; it should be understood that these dimensions are for purposes of illustration only, and variations may be made therein without departing from the scope and spirit of the invention.

The curet shown in FIG. 1 is typically 8 inches in length. It has a distal end portion, 10, which is about 3½ to 4½ inches in length; a tapered shank, 12, about 3½ inches and a proximal end portion, 14, about 1 inch long. A lumen or hollow portion of the curet is shown in phantom and bears legend 16. In the tip region of the distal end portion are a pair of tip openings, 18 and 20, positioned in opposition, i.e. on opposite sides of the curet wall, and displaced from one another. The former opening, 18, is a macerator and the latter, 20, is semi-round. The macerator opening, 18, is located close to the tip and the rounded one, 20, is on the opposite side and positioned further from the end. The positioning of the two openings, and the design of a macerator and rounded openings have a number of advantageous consequences. The macerator assures proper scraping action, and both openings bring about rapid fluid and tissue removal. This rapid removal of loosened tissue by opening 18 is extremely important, as this tends to minimize blood loss and trauma. The opposed tip openings combined with the flexibility of the distal end portion and the rounded tip at 22, tend to minimize accidental perforation. If the curet is pressed too hard against the tissue, there is a tendency for the tip not to proceed and perforate, but to fold over at that portion of the curet between the two openings, 18 and 20.

The proximal end, 14, has a slight outside slope which is adapted to fit onto a hose connected to a source of vacuum or onto any other source of suction. Its diameter typically is 0.532 inches where it joins the tapered portion, 12, and slopes down to approximately 0.500 inches at its end. While a slope fitting is shown in this Figure, any other convenient or conventional fitting may be used which provides a suitable connection to a vacuum source.

The outside diameter of the distal end portion, 10, is dictated by the surgical procedure. Curets typically come in several sizes, the most common have outside diameters of 4 mm, 6 mm, 8 mm and 10 mm. In English units, this is roughly equivalent to 0.157, 0.236, 0.304 and 0.393 inches respectively. The outside taper of the tapered portion, 12, is partially determined by the diameter of the distal end portion, 10. Thus, for example, in a "4 mm" curet, the tapered portion would have its outside diameter increase from approximately 0.157 inches where it joins the distal end portion, 10, to approximately 0.500 inch where it joins the proximal end portion. As shown in the drawings, there is a slight necking-in at the latter joint.

The lumen, 16, increases in diameter from the distal to proximal ends. For example, with a 4 mm curet, the diameter of the lumen (1) near the distal tip is typically 0.100 inches; (2) where the distal end portion, 10, joins the tapered portion, 12, is typically 0.117 inches; and (3) at the other end of the tapered portion, 12, where it joins the proximal end portion, 14, is in the order of 0.300 to 0.400 inches. The wall thickness in the distal end portion, 10, is minimal, consistent with the material of the curet. This provides (1) flexibility, thus lessening possible unwanted perforation during a procedure and (2) minimal outside diameter with maximal internal lumen, with the resulting decreased trauma, which directly follows from the smallest possible outside diameter. The inside diameter, of course, being large enough to carry off the required amount of fluids and semisolids.

Over the tapered central portion there is not the requirement of reducing trauma and a small outside diameter is not essential, as this portion is typically, during uterine aspiration, in a large vaginal area, rather than in the narrow cervex. A certain rigidity moreover is important to enable the surgeon to have a good "feel" and to firmly control the distal end portion of the curet. This is achieved by increasing the thickness of the curet wall in the tapered portion. In the above example the wall thickness increases from 0.020 to approximately 0.100 inches.

The curet itself is preferably made of moldable plastic, such as polyvinyl chloride, polyethylene or polyvinylcarbide. Alternatively, any convenient or conventional moldable plastic compatable for surgical use may be employed. The curet of the present invention may be molded in a single molding step, e.g. by injection molding. The increase in the lumen diameter from the distal end to the proximal end facilitates the use of this single-molding step, and specifically the stripping of the curet from the mold. With a lumen of constant internal diameter, it is difficult to use single molding techniques. The consequence of being able to use this manufacturing technique—one which lends itself to automation—is to greatly reduce the cost of manufacture.

Referring now to the drawing of FIG. 2, there is shown schematically a curet similar to the curet of FIG. 1, however, whose lumen, 26, is of substantially constant diameter. It has a tapered shank, 28, and enjoys a flexible distal end portion with a more rigid tapered shank portion. It has only one opening, 30, at the distal end portion.

FIG. 3 is a schematic diagram of an alternative embodiment of the tip openings. Here there are two rounded tip openings, 32 and 34, in opposition to each other, but equally spaced from the end of the curet. The advantage of this arrangement is that the curet will tend to fold over at the end portion region, rather than be rigid enough to perforate through the uterine wall.

Variations may be made in the tip openings. For example—disposition of the openings; one, or more than two openings; and openings of different configurations.

FIG. 4 shows in detail the tip opening of the curet of FIG. 1. Focusing first on the macerator opening 18 it should be noted that its cutting edge 48 is inclined slightly (approximately 10 degrees) from a plane perpendicular to the central line or axis of the curet. The edge at the outer wall is sharp enough to scrape tissue from the soft uterine wall. During the extraction of tissue for diagnostic purposes (e.g., the sampling of tissue from the endometrium) it is desirable that the area or the cross section of the macerator opening be fairly large. For example, in a 4 mm curet the length of the opening L in the drawing of FIG. 4 should be approximately =10 mm. The transverse portion of the opening being half round =extending to the center line of the curet. I.e., the distance C as shown in the drawing is approximately 2 mm. The portion of the curetting opening closest to the handle or proximal end of the curet may be rounded smooth and shown here typically having a radius R which is approximately 1½ times the outside diameter of the curet, in this example 6 mm. The cross sectional area of the tip opening 10, i.e. the open area of the lumen exposed to the wall of the uterus during a procedure is approximately 8 to 12 times the outside diameter in square millimeters ($mm^2$). This large cross sectional area of the macerator facilitates the extraction of the tissue. This large cross sectional area is especially important when the curet is used with an initial high vacuum, e.g., 0.2 atmospheres and higher. Some variation may be made in the details of the macerator opening 18. However, the combination of an opening with a macerator (i.e., scraping edge) and a large opening (i.e., large cross section area) should go together. A typical curet would be as follows.

| Curet Size | L | C | R | Approximate Area |
|---|---|---|---|---|
| 3mm | 10mm | 1.5mm | 5mm | 25mm$^2$ |
| 4mm | 10mm | 2mm | 6mm | 32mm$^2$ |
| 5mm | 11mm | 2.5mm | 7.5mm | 45mm$^2$ |
| 6mm | 12mm | 3mm | 9mm | 72mm$^2$ |

The center line of the second tip opening 20 is typically located a distance approximately 5 times the outside curet diameter from the detal end. This opening may be uniformly curved and extend into the curet up to the center line thereof and for a 4 mm curet have a radius of approximately 12.5 mm. This is a typical dimension which would also be applicable for a 3, 5, or 6 mm curet.

The material of the curet is preferably a transparent plastic. In diagnostics this is important as it permits the surgeon to observe in that portion of the curet which is visible during a procedure, the blood and other items which are extracted from the uterus or endometrium. Particularly this partially advises the surgeon as to whether or not he has enough material extracted from the endometrium for suitable sampling, or if he is producing a large flow, which may be undesirable. Many of the prior art diagnostic curets are made of steel, not transparent, and it is impossible to make the observation as to both the quantity and nature of the material being collected. The wall thickness (wt in the FIG. 4) typically is 0.025 inches to 0.040 inches. It should preferably, as noted above, be as thin as possible yet consistent with the mechanical requirements.

The macerator opening 18 having both the cutting edge and a large cross sectional area may be used in curets of various designs, and may have variations made therein. As noted above, there may be one opening of more than two openings. Moreover, it may be used with curets of various designs, with both tapered and straight and other varieties of shanks.

The invention has been described with a specific example giving particular dimensions. It should be understood that these dimensions are for purposes of illustration only and that various modifications may be made therefrom without departing from the scope and spirit of the invention.

I claim:

1. A curet for use in sampling tissue from the uterus with an initial high vacuum, e.g. higher than 0.2 atm., comprising a tube of flexible material having a distal end portion adapted to be inserted into the uterus, and a proximal end portion adapted to be connected to a high vacuum source, and an intermediate shank; said distal portion having at its tip region at least a pair of tip openings opposed to one another; one of said tip openings being rounded when viewed from a side plane parallel to the curet longitudinal axis, and the other being a macerator, said macerator opening being closer to the tip than the round one, and having an open cross section area of the lumen approximately 8 to 12 times the outside diameter of said curet in the distal portion; said macerator open cross section area further comprising three portions; a large central portion extending in a plane substantially parallel to and through the axis of the curet and having a length along the axis of approximately 10 to 12 mm, a cutting edge portion beginning at the distal end of said central portion and inclined slightly from a plane perpendicular to the axis of the curet toward the proximal end; and a rounded smooth portion beginning in said plane substantially through the axis of the curet and extending to the outer wall away from said plane in a half-round shape with a radius which is approximately one-and-one-half times the outside diameter of the curet, and said curet wall thickness in the region of said opening being approximately 0.025 inches to 0.04 inches.

2. A curet according to claim 1 having an outside diameter of approximately 4 mm, said macerator having its cutting edge towards said tip, and an open cross-section of approximately 32 mm$^2$.

3. A curet according to claim 1 having an outside diameter of approximately 3 mm, said macerator having its cutting edge towards said tip, and an open cross-section of approximately 25 mm$^2$.

4. A curet according to claim 1 having an outside diameter of approximately 5 mm, said macerator having its cutting edge towards said tip, and an open cross-section of approximately 45 mm$^2$.

5. A curet according to claim 1 having an outside diameter of approximately 6 mm said macerator having its cutting edge towards said tip, and an open cross-section of approximately 72 mm$^2$.

6. A curet according to claim 1 wherein said curet is transparent at least in its shank region.

7. A curet according to claim 1, wherein said curet is a single piece of molded plastic.

8. A curet for use in sampling tissue from the uterus with an initial high vacuum, e.g., higher than 0.2 atm., comprising a tube of flexible material having a distal end portion adapted to be inserted into the uterus, and a proximal end portion adapted to be connected to a high vacuum source, and an intermediate shank; said distal portion having at its tip region at least a pair of tip openings opposed to one another; one of said tip openings being rounded when viewed from a side plane parallel to the curet longitudinal axis, and the other being a macerator, said macerator opening being closer to the tip than the round one, and having a cross section area approximately 11 to 18 times the diameter of the lumen, i.e., the inside diameter of said curet in the distal portion; said macerator opening further comprising three portions; a large central portion extending in a plane substantially parallel to and through the axis of the curet, a cutting edge portion beginning at the distal end of said central portion and inclined slightly from a plane perpendicular to the axis of the curet toward the proximal end; and a rounded smooth portion beginning in said plane substantially through the axis of the curet and extending to the outer wall away from said plane in a half-round shape with a radius which is approximately one-and-one-half times the outside diameter of the curet.

9. A curet according to claim 8 wherein said curet is transparent at least in its shank.

10. A curet according to claim 8, wherein said flexible material is a single piece of molded plastic.

11. A curet according to claim 8 having an outside diameter of approximately 4 mm, said macerator having its cutting edge towards said tip, and an open cross-section of approximately 32 mm$^2$.

12. A curet according to claim 8 having an outside diameter of approximately 3 mm, said macerator having its cutting edge towards said tip, and an open cross-section of approximately 25 mm$^2$.

13. A curet according to claim 8 having an outside diameter of approximately 5 mm, said macerator having its cutting edge towards said tip, and an open cross-section of approximately 45 mm$^2$.

14. A curet according to claim 8 having an outside diameter of approximately 6 mm said macerator having its cutting edge towards said tip, and an open cross-section of approximately 72 mm$^2$.

* * * * *